(12) United States Patent
Guo et al.

(10) Patent No.: US 9,834,529 B2
(45) Date of Patent: Dec. 5, 2017

(54) SYNTHESIS OF BENZOTHIAZEPINES

(71) Applicant: GlaxoSmithKline Intellectual Property (No.2) Limited, Brentford, Middlesex (GB)

(72) Inventors: Jiasheng Guo, Research Triangle Park, NC (US); Bing Liu, Research Triangle Park, NC (US); Mark B. Mitchell, Research Triangle Park, NC (US); Michael T. Martin, Research Triangle Park, NC (US); Xiaoming Zhou, Research Triangle Park, NC (US)

(73) Assignee: GLAXOSMITHKLINE INTELLECTUAL PROPERTY (NO. 2) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/500,619

(22) PCT Filed: Jul. 23, 2015

(86) PCT No.: PCT/IB2015/055584
§ 371 (c)(1),
(2) Date: Jan. 31, 2017

(87) PCT Pub. No.: WO2016/020785
PCT Pub. Date: Feb. 11, 2016

(65) Prior Publication Data
US 2017/0210717 A1    Jul. 27, 2017

Related U.S. Application Data

(60) Provisional application No. 62/033,181, filed on Aug. 5, 2014.

(51) Int. Cl.
*C07D 281/10*    (2006.01)

(52) U.S. Cl.
CPC .................... *C07D 281/10* (2013.01)

(58) Field of Classification Search
CPC ....................................... C07D 281/10
USPC ........................................... 540/552
See application file for complete search history.

(56) References Cited

FOREIGN PATENT DOCUMENTS

WO      WO 96/05188 A      2/1996
WO      WO 2011/137135 A1  11/2011

OTHER PUBLICATIONS

Cowan, et al. Journal of Organic Chemistry, 78: 12726-12734 (Nov. 20, 2013).
Wu, et al. Journal of Medicinal Chemistry, 56: 5094-5114 (May 16, 2013).

*Primary Examiner* — Brenda Coleman
(74) *Attorney, Agent, or Firm* — Robert H. Brink; Edward R. Gimmi; William R. Majarian

(57) ABSTRACT

Methods for preparing the following compound are disclosed.

10 Claims, No Drawings

SYNTHESIS OF BENZOTHIAZEPINES

This application is a §371 of International Application No. PCT/IB2015/055584, filed 23 Jul. 2015, which claims the benefit of U.S. Provisional Application No. 62/033,181, filed 5 Aug. 2014, which are incorporated herein in their entireties.

FIELD OF THE INVENTION

The present invention relates to improved synthetic methods for certain compounds that are useful in the treatment and prevention of metabolic disorders, including diabetes mellitus (Type I and Type II), obesity, and related disorders.

BACKGROUND OF THE INVENTION

More than 200 million people worldwide have diabetes. The World Health Organization estimates that 1.1 million people died from diabetes in 2005 and projects that worldwide deaths from diabetes will double between 2005 and 2030. New chemical compounds that effectively treat diabetes could save millions of human lives.

Diabetes refers to metabolic disorders resulting in the body's inability to effectively regulate glucose levels. Approximately 90% of all diabetes cases are a result of type 2 diabetes whereas the remaining 10% are a result of type 1 diabetes, gestational diabetes, and latent autoimmune diabetes of adulthood (LADA). All forms of diabetes result in elevated blood glucose levels and, if left untreated chronically, can increase the risk of macrovascular (heart disease, stroke, other forms of cardiovascular disease) and microvascular [kidney failure (nephropathy), blindness from diabetic retinopathy, nerve damage (diabetic neuropathy)] complications.

Type 1 diabetes, also known as juvenile or insulin-dependent diabetes mellitus (IDDM), can occur at any age, but it is most often diagnosed in children, adolescents, or young adults. Type 1 diabetes is caused by the autoimmune destruction of insulin-producing beta cells, resulting in an inability to produce sufficient insulin. Insulin controls blood glucose levels by promoting transport of blood glucose into cells for energy use. Insufficient insulin production will lead to decreased glucose uptake into cells and result in accumulation of glucose in the bloodstream. The lack of available glucose in cells will eventually lead to the onset of symptoms of type 1 diabetes: polyuria (frequent urination), polydipsia (thirst), constant hunger, weight loss, vision changes, and fatigue. Within 5-10 years of being diagnosed with type 1 diabetes, patient's insulin-producing beta cells of the pancreas are completely destroyed, and the body can no longer produce insulin. As a result, patients with type 1 diabetes will require daily administration of insulin for the remainder of their lives.

Type 2 diabetes, also known as non-insulin-dependent diabetes mellitus (NIDDM) or adult-onset diabetes, occurs when the pancreas produces insufficient insulin and/or tissues become resistant to normal or high levels of insulin (insulin resistance), resulting in excessively high blood glucose levels. Multiple factors can lead to insulin resistance including chronically elevated blood glucose levels, genetics, obesity, lack of physical activity, and increasing age. Unlike type 1 diabetes, symptoms of type 2 diabetes are more salient, and as a result, the disease may not be diagnosed until several years after onset with a peak prevalence in adults near an age of 45 years. Unfortunately, the incidence of type 2 diabetes in children is increasing.

The primary goal of treatment of type 2 diabetes is to achieve and maintain glycemic control to reduce the risk of microvascular (diabetic neuropathy, retinopathy, or nephropathy) and macrovascular (heart disease, stroke, other forms of cardiovascular disease) complications. Current guidelines for the treatment of type 2 diabetes from the American Diabetes Association (ADA) and the European Association for the Study of Diabetes (EASD) [*Diabetes Care*, 2008, 31 (12), 1] outline lifestyle modification including weight loss and increased physical activity as a primary therapeutic approach for management of type 2 diabetes. However, this approach alone fails in the majority of patients within the first year, leading physicians to prescribe medications over time. The ADA and EASD recommend metformin, an agent that reduces hepatic glucose production, as a Tier 1a medication; however, a significant number of patients taking metformin can experience gastrointestinal side effects and, in rare cases, potentially fatal lactic acidosis. Recommendations for Tier 1b class of medications include sulfonylureas, which stimulate pancreatic insulin secretion via modulation of potassium channel activity, and exogenous insulin. While both medications rapidly and effectively reduce blood glucose levels, insulin requires 1-4 injections per day and both agents can cause undesired weight gain and potentially fatal hypoglycemia. Tier 2a recommendations include newer agents such as thiazolidinediones (TZDs pioglitazone and rosiglitazone), which enhance insulin sensitivity of muscle, liver and fat, as well as GLP-1 analogs, which enhance postprandial glucose-mediated insulin secretion from pancreatic beta cells. While TZDs show robust, durable control of blood glucose levels, adverse effects include weight gain, edema, bone fractures in women, exacerbation of congestive heart failure, and potential increased risk of ischemic cardiovascular events. GLP-1 analogs also effectively control blood glucose levels, however, this class of medications requires injection and many patients complain of nausea. The most recent addition to the Tier 2 medication list is DPP-4 inhibitors, which, like GLP-1 analogs, enhance glucose-medicated insulin secretion from beta cells. Unfortunately, DPP-4 inhibitors only modestly control blood glucose levels, and the long-term safety of DPP-4 inhibitors remains to be firmly established. Other less prescribed medications for type 2 diabetes include α-glucosidase inhibitors, glinides, and amylin analogs. Clearly, new medications with improved efficacy, durability, and side effect profiles are needed for patients with type 2 diabetes.

GLP-1 and GIP are peptides, known as incretins, that are secreted by L and K cells, respectively, from the gastrointestinal tract into the blood stream following ingestion of nutrients. This important physiological response serves as the primary signaling mechanism between nutrient (glucose/fat) concentration in the gastrointestinal tract and other peripheral organs. Upon secretion, both circulating peptides initiate signals in beta cells of the pancreas to enhance glucose-stimulated insulin secretion, which, in turn, controls glucose concentrations in the blood stream (For reviews see: *Diabetic Medicine* 2007, 24(3), 223; *Molecular and Cellular Endocrinology* 2009, 297(1-2), 127; *Experimental and Clinical Endocrinology & Diabetes* 2001, 109 (Suppl. 2), S288).

The association between the incretin hormones GLP-1 and GIP and type 2 diabetes has been extensively explored. The majority of studies indicate that type 2 diabetes is associated with an acquired defect in GLP-1 secretion as well as GIP action (see *Diabetes* 2007, 56(8), 1951 and *Current Diabetes Reports* 2006, 6(3), 194). The use of exogenous GLP-1 for treatment of patients with type 2 diabetes is severely limited due to its rapid degradation by the protease DPP-4. Multiple modified peptides have been designed as GLP-1 mimetics that are DPP-4 resistant and show longer half-lives than endogenous GLP-1. Agents with this profile that have been shown to be highly effective for treatment of type 2 diabetes include exenatide and liraglutide, however, these agents require injection. Oral agents that inhibit DPP-4, such as sitagliptin vildagliptin, and saxagliptin, elevate intact GLP-1 and modestly control circulating glucose levels (see *Pharmacology & Therapeutics* 2010, 125(2), 328; *Diabetes Care* 2007, 30(6), 1335; *Expert Opinion on Emerging Drugs* 2008, 13(4), 593). New oral medications that increase GLP-1 secretion would be desirable for treatment of type 2 diabetes.

Bile acids have been shown to enhance peptide secretion from the gastrointestinal tract. Bile acids are released from the gallbladder into the small intestine after each meal to facilitate digestion of nutrients, in particular fat, lipids, and lipid-soluble vitamins. Bile acids also function as hormones that regulate cholesterol homeostasis, energy, and glucose homeostasis via nuclear receptors (FXR, PXR, CAR, VDR) and the G-protein coupled receptor TGR5 (for reviews see: *Nature Drug Discovery* 2008, 7, 672; *Diabetes, Obesity and Metabolism* 2008, 10, 1004). TGR5 is a member of the Rhodopsin-like subfamily of GPCRs (Class A) that is expressed in intestine, gall bladder, adipose tissue, liver, and select regions of the central nervous system. TGR5 is activated by multiple bile acids with lithocholic and deoxycholic acids as the most potent activators (*Journal of Medicinal Chemistry* 2008, 51(6), 1831). Both deoxycholic and lithocholic acids increase GLP-1 secretion from an enteroendocrine STC-1 cell line, in part through TGR5 (*Biochemical and Biophysical Research Communications* 2005, 329, 386). A synthetic TGR5 agonist INT-777 has been shown to increase intestinal GLP-1 secretion in vivo in mice (*Cell Metabolism* 2009, 10, 167). Bile salts have been shown to promote secretion of GLP-1 from colonic L cells in a vascularly perfused rat colon model (*Journal of Endocrinology* 1995, 145(3), 521) as well as GLP-1, peptide YY (PYY), and neurotensin in a vascularly perfused rat ileum model (*Endocrinology* 1998, 139(9), 3780). In humans, infusion of deoxycholate into the sigmoid colon produces a rapid and marked dose responsive increase in plasma PYY and enteroglucagon concentrations (*Gut* 1993, 34(9), 1219). Agents that increase ileal and colonic bile acid or bile salt concentrations will increase gut peptide secretion including, but not limited to, GLP-1 and PYY.

Bile acids are synthesized from cholesterol in the liver then undergo conjugation of the carboxylic acid with the amine functionality of taurine and glycine. Conjugated bile acids are secreted into the gall bladder where accumulation occurs until a meal is consumed. Upon eating, the gall bladder contracts and empties its contents into the duodenum, where the conjugated bile acids facilitate absorption of cholesterol, fat, and fat-soluble vitamins in the proximal small intestine (For reviews see: *Frontiers in Bioscience* 2009, 14, 2584; *Clinical Pharmacokinetics* 2002, 41(10), 751; *Journal of Pediatric Gastroenterology and Nutrition* 2001, 32, 407). Conjugated bile acids continue to flow through the small intestine until the distal ileum where 90% are reabsorbed into enterocytes via the apical sodium-dependent bile acid transporter (ASBT, also known as iBAT). The remaining 10% are deconjugated to bile acids by intestinal bacteria in the terminal ileum and colon of which 5% are then passively reabsorbed in the colon and the remaining 5% being excreted in feces. Bile acids that are reabsorbed by ASBT in the ileum are then transported into the portal vein for recirculation to the liver. This highly regulated process, called enterohepatic recirculation, is important for the body's overall maintenance of the total bile acid pool as the amount of bile acid that is synthesized in the liver is equivalent to the amount of bile acids that are excreted in feces. Pharmacological disruption of bile acid reabsorption with an inhibitor of ASBT leads to increased concentrations of bile acids in the colon and feces, a physiological consequence being increased conversion of hepatic cholesterol to bile acids to compensate for fecal loss of bile acids. Many pharmaceutical companies have pursued this mechanism as a strategy for lowering serum cholesterol in patients with dyslipidemia/hypercholesterolemia (For a review see: *Current Medicinal Chemistry* 2006, 13, 997). Importantly, ASBT-inhibitor mediated increase in colonic bile acid/salt concentration also will increase intestinal GLP-1, PYY, GLP-2, and other gut peptide hormone secretion. Thus, inhibitors of ASBT could be useful for treatment of type 2 diabetes, type 1 diabetes, dyslipidemia, obesity, short bowel syndrome, Chronic Idiopathic Constipation, Irritable bowel syndrome (IBS), Crohn's disease, and arthritis.

Certain 1,4-thiazepines are disclosed, for example in WO 94/18183 and WO 96/05188. These compounds are said to be useful as ileal bile acid reuptake inhibitors (ASBT).

Patent publication WO 2011/137,135 discloses, among other compounds, the following compound. This patent publication also discloses methods of synthesis of the compound.

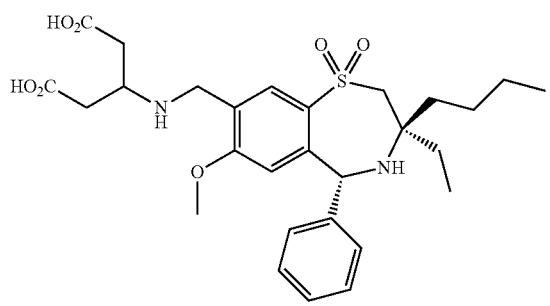 [SMILES: CCCC[C@]1(CC)CS(=O)(=O)c2cc(CNC(CC(=O)O)CC(=O)O)c(OC)cc2[C@@H](c2ccccc2)N1]

The preparation of the above compound is also disclosed in J. Med. Chem, Vol 56, pp 5094-5114 (2013).

SUMMARY OF THE INVENTION

Briefly, in one aspect, the present invention discloses an improved synthesis of the compound

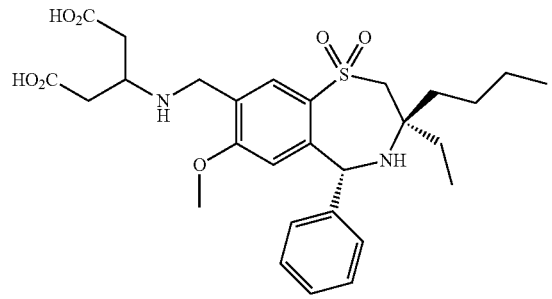 [SMILES: CCCC[C@]1(CC)CS(=O)(=O)c2cc(CNC(CC(=O)O)CC(=O)O)c(OC)cc2[C@@H](c2ccccc2)N1]

comprising the step of preparing the compound (Intermediate H)

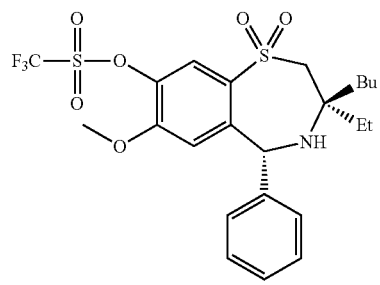

from 3-hydroxy-4-methoxythiophenol (intermediate A).

DETAILED DESCRIPTION OF THE INVENTION

In another aspect, the method of this invention comprises the step of converting 3-hydroxy-4-methoxythiophenol to

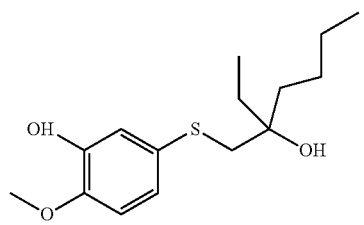 [SMILES: CCCCC(O)(CC)CSc1ccc(OC)c(O)c1]

which is then converted to

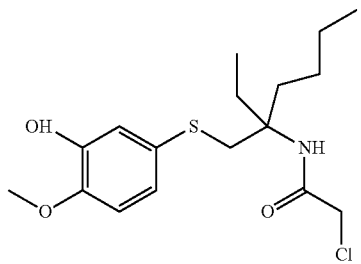 [SMILES: CCCCC(CC)(CSc1ccc(OC)c(O)c1)NC(=O)CCl]

via a Ritter reaction.

Preferably, said Ritter reaction uses ClCH$_2$CN.

In another aspect, the method of this invention comprises the step of converting 3-hydroxy-4-methoxythiophenol to

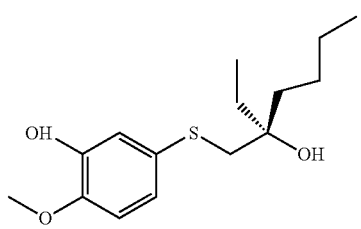

for example, by reaction with (R)-2-ammonio-2-ethylhexyl sulfate.

In one aspect the method of this invention comprises preparation of 3-hydroxy-4-methoxythiophenol from 2-methoxyphenyl acetate, and converting 3-hydroxy-4-methoxythiophenol to

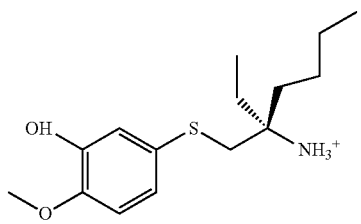 [SMILES: CCCC[C@]([NH3+])(CC)CSc1ccc(OC)c(O)c1]

which is then converted to

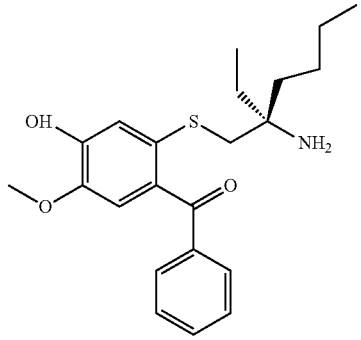 [SMILES: CCCC[C@](N)(CC)CSc1cc(O)c(OC)cc1C(=O)c1ccccc1]

which is then converted to

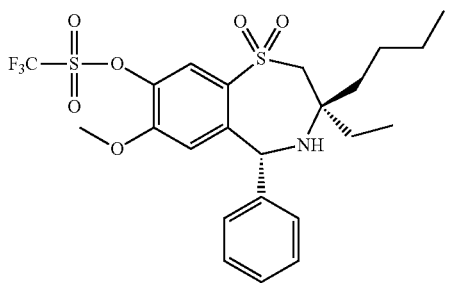 [SMILES: CCCC[C@]1(CC)CS(=O)(=O)c2cc(OS(=O)(=O)C(F)(F)F)c(OC)cc2[C@@H](c2ccccc2)N1]

which is then converted to

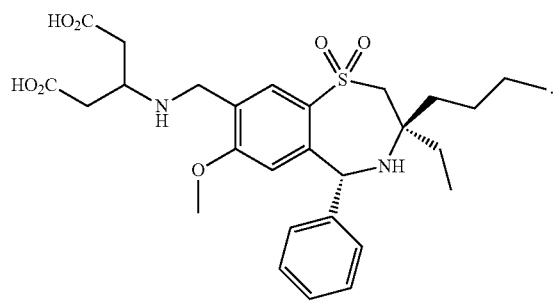 [SMILES: CCCC[C@]1(CC)CS(=O)(=O)c2cc(CNC(CC(=O)O)CC(=O)O)c(OC)cc2[C@@H](c2ccccc2)N1]

EXAMPLES

Patent publication WO 2011/137,135 discloses general methods for preparing the compound. In addition, a detailed synthesis of the compound is disclosed in Example 26. J. Med. Chem, Vol 56, pp 5094-5114 (2013) also discloses a method for synthesising the compound.

The present invention discloses an improved synthesis of the compound.

The synthetic scheme of the present invention is depicted in Scheme 1. Treatment of 2-methoxyphenyl acetate with sulfur monochloride followed by ester hydrolysis and reduction with zinc gave rise to thiophenol (A). Epoxide ring opening of (±)-2-butyl-ethyloxirane with thiophenol (A) and subsequent treatment of tertiary alcohol (B) with chloroacetonitrile under acidic conditions gave chloroacetamide (C), which was then converted to intermediate (E) by cleavage of the chloroacetamide with thiourea followed by classical resolution with dibenzoyl-L-tartaric acid. Benzoylation of intermediate (E) with triflic acid and benzoyl chloride afforded intermediate (H). Cyclization of intermediate (H) followed by oxidation of the sulfide to a sulphone, subsequent imine reduction and classical resolution with (+)-camphorsulfonic acid provided intermediate (G), which was then converted to intermediate (H). Intermediate (H) was converted to the target compound using the methods disclosed in Patent publication WO 2011/137,135.

Scheme 1

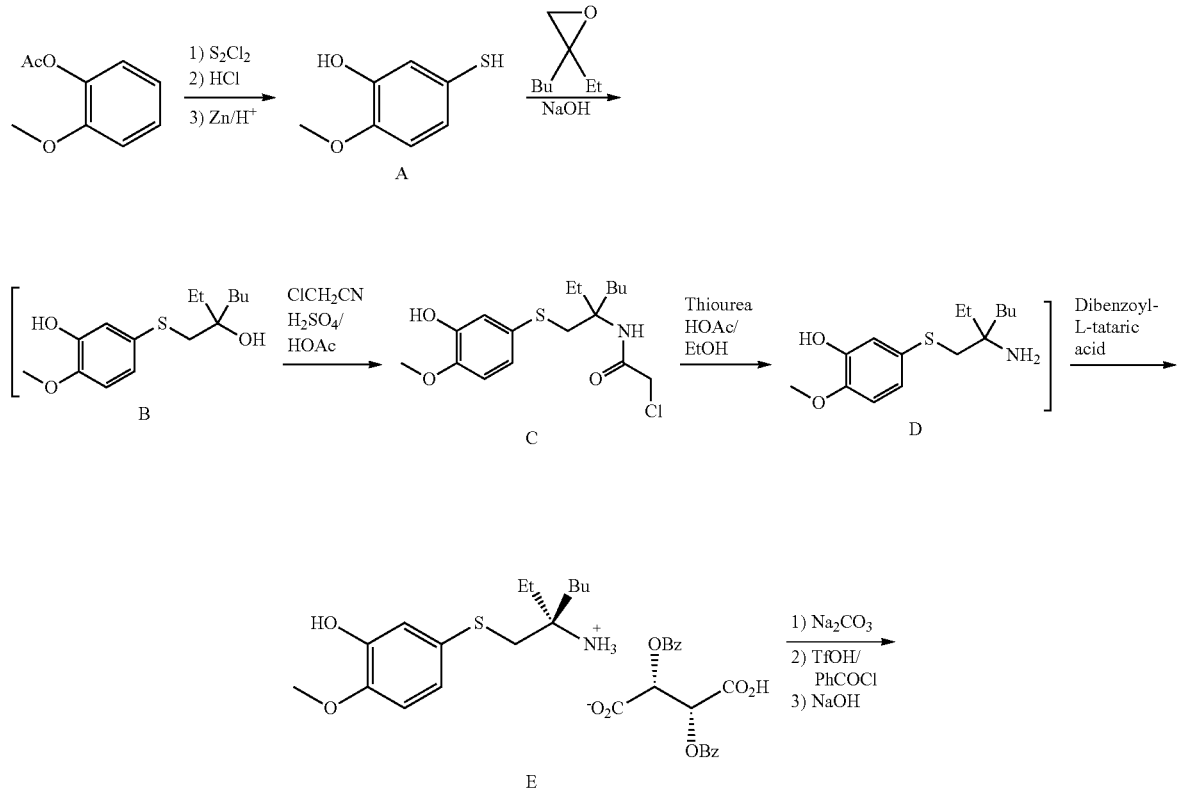

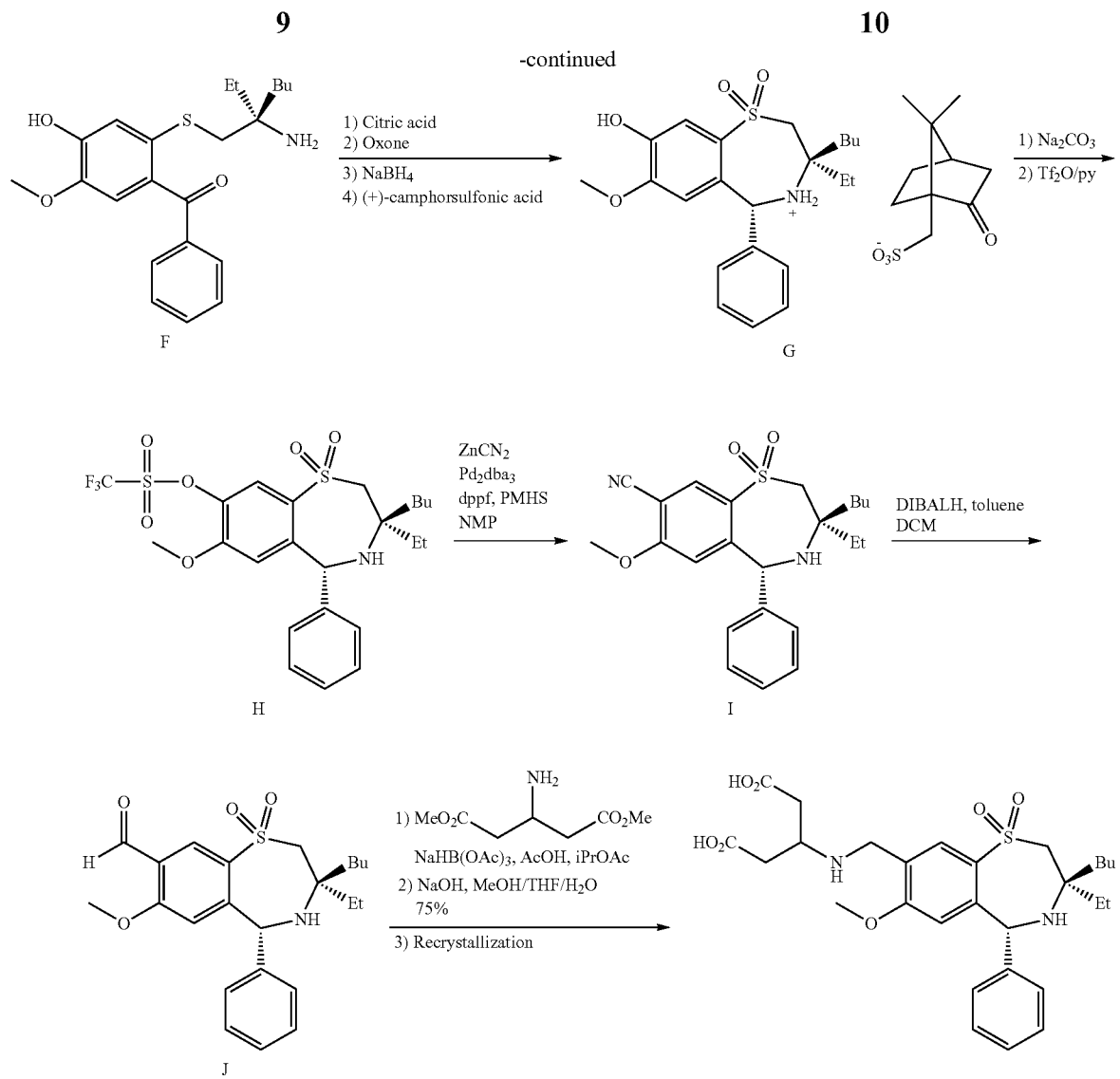
The present invention also discloses an alternative method for construction of the quaternary chiral center as depicted in Scheme 2. Reaction of intermediate (A) with (R)-2-ammonio-2-ethylhexyl sulfate (K) followed by formation of di-p-toluoyl-L-tartrate salt furnished intermediate (L).
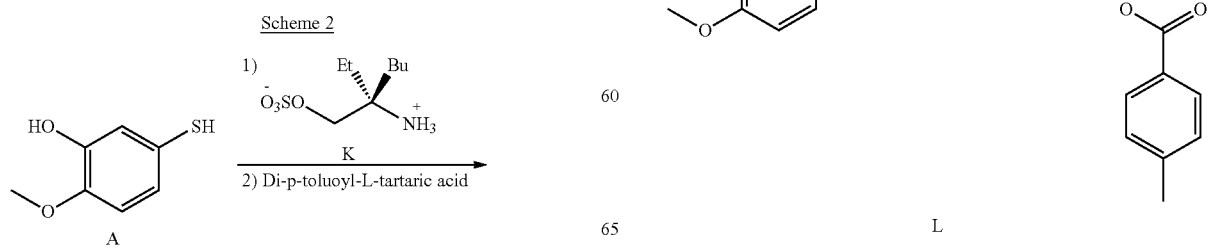

The present invention also discloses an alternative synthesis of intermediate (H) as illustrated in Scheme 3. Acid catalyzed cyclization of intermediate (F) followed by triflation gave imine (M), which underwent asymmetric reduction with catalyst Ir(COD)$_2$BArF and ligand (N) to give intermediate (O). Oxidation of the sulfide in intermediate (O) gave sulphone intermediate (H).

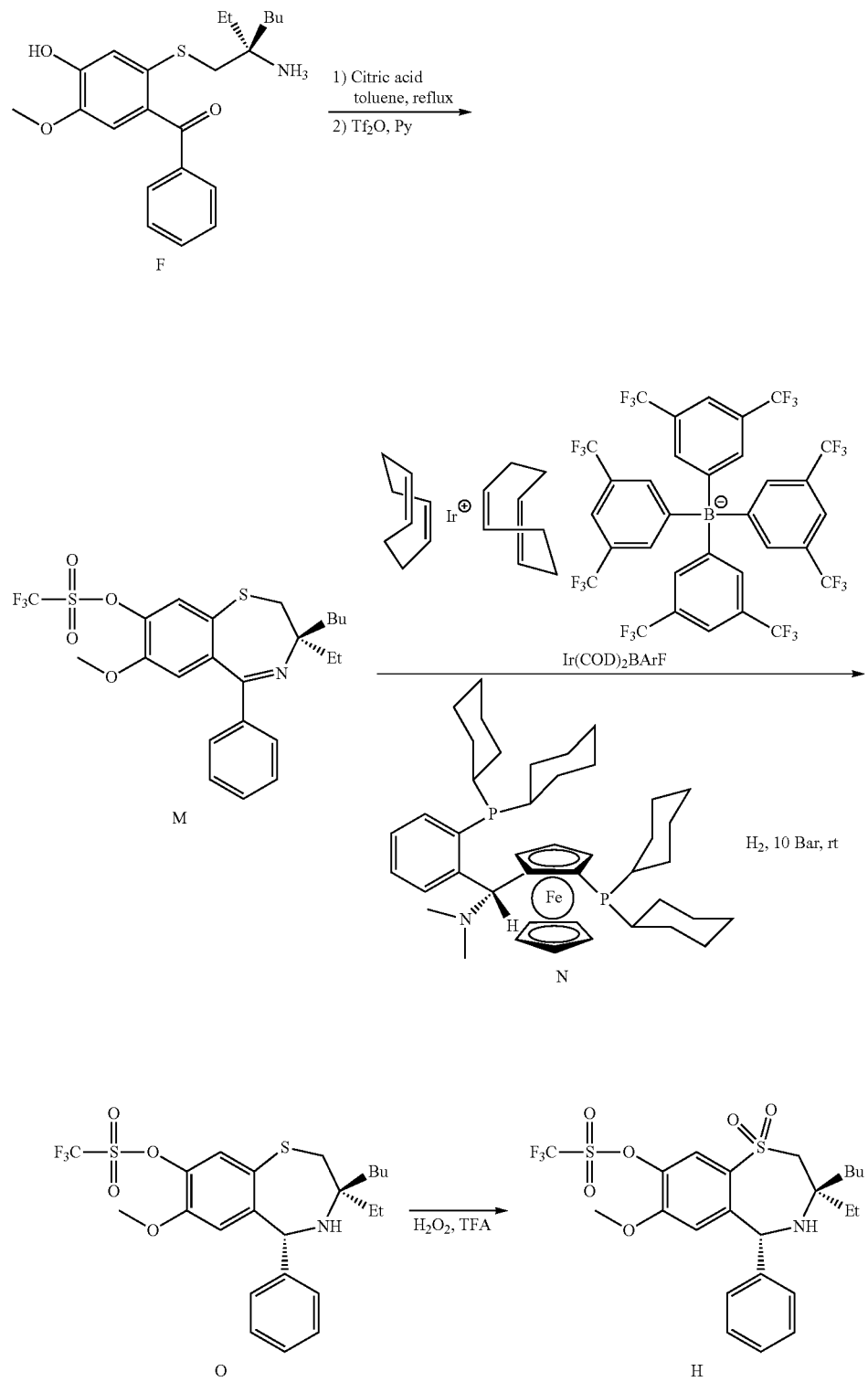

Scheme 3

The present invention differs from the synthesis disclosed in WO 2011/137,135 and J. Med. Chem, Vol 56, pp 5094-5114 (2013) in that intermediate (H) in the present invention is prepared via a new, shorter and more cost-efficient synthesis while the synthesis of the target compound from intermediate (H) remains unchanged.

Advantages of the Present Invention

1) In the improved synthesis the number of synthetic steps is reduced.
2) The improved synthesis is significantly more cost-efficient.
3) The improved synthesis does not require any chromatographic purification.

ABBREVIATIONS

Bz Benzoyl
TfOH Trifluoromethanesulfonic acid
PhCOCl Benzoyl chloride
Tf$_2$O Trifluoroacetic anhydride
Py Pyridine
DME Dimethoxyethane
MTBE Methyl t-butyl ether
EtOAc Ethyl acetate
HOAc Acetic acid
EtOH Ethanol
MeCN Acetonitrile
DCM Dichloromethane Intermediate A: 3-Hydroxy-4-methoxythiophenol

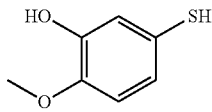

A reaction vessel was charged with 2-methoxyphenyl acetate (60 g, 0.36 mol), zinc chloride (49.2 g, 0.36 mol) and DME (600 mL). The mixture was stirred and S$_2$Cl$_2$ (53.6 g, 0.40 mol) was added. The mixture was stirred at ambient temperature for 2 h. Concentrated HCl (135.4 mL, 1.63 mol) was diluted with water (60 mL) and added slowly to the rxn mixture, maintaining the temperature below 60° C. The mixture was stirred at 60° C. for 2 h and then cooled to ambient temperature. Zinc dust (56.7 g, 0.87 mol) was added in portions, maintaining the temperature below 60° C. The mixture was stirred at 20-60° C. for 1 h and then concentrated under vacuum to ~300 mL. MTBE (1.2 L) and water (180 mL) were added and the mixture was stirred for 10 min. The layers were separated and the organic layer was washed twice with water (2×240 mL). The layers were separated and the organic layer was concentrated under vacuum to give an oil. The oil was distilled at 110-115° C./2 mbar to give the title compound (42 g, 75%) as colorless oil, which solidified on standing to afford the title compound as a white solid. M.P. 41-42° C. $^1$H NMR (500 MHz, CDCl$_3$)#5 ppm 3.39 (s, 1H), 3.88 (s, 3H), 5.65 (br. S, 1H), 6.75 (d, J=8.3 Hz, 1H), 6.84 (ddd, J=8.3, 2.2, 0.6 Hz, 1H), 6.94 (d, J=2.2 Hz).

Intermediate E: (R)-5-((2-amino-2-ethylhexyl)thio)-2-methoxyphenol, dibenzoyl-L-tartrate salt

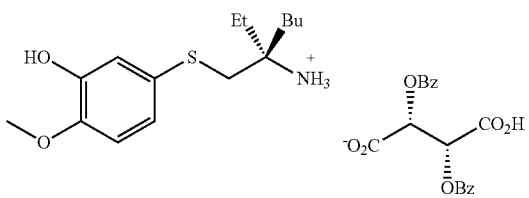

A reaction vessel was charged with 3-hydroxy-4-methoxythiophenol (5.0 g, 25.2 mmol), (±)-2-butyl-2-ethyl-oxirane (3.56 g, 27.7 mmol) and EtOH (30 mL). The mixture was treated with a solution of NaOH (2.22 g, 55.5 mmol) in water (20 mL), heated to 40° C. and stirred at 40° C. for 5 h. The mixture was cooled to ambient temperature, treated with toluene (25 mL) and stirred for 10 min. The layers were separated and the organic layer was discarded. The aqueous layer was neutralized with 2 N HCl (27.8 mL, 55.6 mmol) and extracted with toluene (100 mL). The organic layer was washed with water (25 mL), concentrated in vacuo to give an oil. The oil was treated with chloroacetonitrile (35.9 mL) and HOAc (4.3 mL) and cooled to 0° C. H$_2$SO$_4$ (6.7 mL, 126 mmol, pre-diluted with 2.3 mL of water) was added at a rate maintaining the temperature below 10° C. After stirred at 0° C. for 0.5 h, the reaction mixture was treated with 20% aqueous Na$_2$CO$_3$ solution to adjust the pH to 7-8 and then extracted with MTBE (70 mL). The extract was washed with water (35 mL) and concentrated in vacuo to give an oil. The oil was then dissolved in EOH (50 mL) and treated with HOAc (10 mL) and thiourea (2.30 g, 30.2 mmol). The mixture was heated at reflux overnight and then cooled to ambient temperature. The solids were filtered and washed with EtOH (10 mL). The filtrate and the wash were combined and concentrated in vacuo, treated with MTBE (140 mL) and washed successively with 10% aqueous Na$_2$CO$_3$ and water. The mixture was concentrated in vacuo to give an oil. The oil was dissolved in MeCN (72 mL), heated to ~50° C. and then dibenzoyl-L-tartaric acid (9.0 g, 25.2 mmol) in acetonitrile (22 mL) was added slowly. Seed crystals were added at ~50° C. The resultant slurry was stirred at 45-50° C. for 5 h, then cooled down to ambient temperature and stirred at ambient temperature overnight. The solids were filtered and washed with MeCN (2×22 mL). The wet cake was treated with MeCN (150 mL) and heated to 50° C. The slurry was stirred at 50° C. for 5 h, cooled over 1 h to ambient temperature and stirred at ambient temperature overnight. The solids were collected by filtration, washed with MeCN (2×20 mL), dried under vacuum to give the title compound (5.5 g, 34% overall yield, 99.5% purity, 93.9% ee) as a white solid. ¹H NMR (500 MHz, DMSO-d₆) δ ppm 0.78 (m, 6H), 1.13 (m, 4H), 1.51 (m, 2H), 1.58 (q, J=7.7 Hz, 2H), 3.08 (s, 2H), 3.75 (s, 3H), 5.66 (s, 2H), 6.88 (m, 2H), 6.93 (m, 1H), 7.49 (m, 4H), 7.63 (m, 2H), 7.94 (m, 4H). EI-LCMS m/z 284 (M⁺+1 of free base).

Intermediate F: (R)-(2-((2-amino-2-ethylhexyl)thio)-4-hydroxy-5-methoxyphenyl)(phenyl)methanone

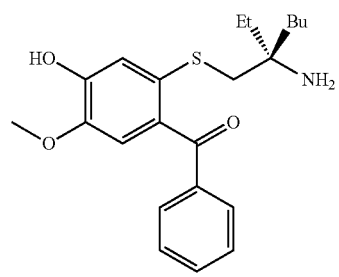

A suspension of (R)-5-((2-amino-2-ethylhexyl)thio)-2-methoxyphenol, dibenzoyl-L-tartrate salt (29 g, 45.2 mmol) in DCM (435 mL) was treated with water (116 mL) and 10% aqueous Na₂CO₃ solution (116 mL). The mixture was stirred at ambient temperature until all solids were dissolved (30 min). The layers were separated. The organic layer was washed with water (2×60 mL), concentrated under vacuum to give (R)-5-((2-amino-2-ethylhexyl)thio)-2-methoxyphenol (free base) as an off-white solid (13.0 g, quantitative). A vessel was charged with TfOH (4.68 ml, 52.9 mmol) and DCM (30 mL) and the mixture was cooled to 0° C. 5 g (17.6 mmol) of (R)-5-((2-amino-2-ethylhexyl)thio)-2-methoxyphenol (free base) was dissolved in DCM (10 mL) and added at a rate maintaining the temperature below 10° C. Benzoyl chloride (4.5 mL, 38.8 mmol) was added at a rate maintaining the temperature below 10° C. The mixture was then heated to reflux and stirred at reflux for 48 h. The mixture was cooled to 30° C. Water (20 mL) was added and the mixture was concentrated to remove DCM. EtOH (10 mL) was added. The mixture was heated to 40° C., treated with 50% aqueous NaOH solution (10 mL) and stirred at 55° C. After 1 h, the mixture was cooled to ambient temperature and the pH was adjusted to 6-7 with conc. HCl. The mixture was concentrated in vacuo to remove EtOH. EtOAc (100 mL) was added. The mixture was stirred for 5 min and the layers were separated. The organic layer was washed successively with 10% aqueous Na₂CO₃ (25 mL) and water (25 mL) and then concentrated in vacuo. The resultant oil was treated with DCM (15 mL). The resultant thick slurry was further diluted with DCM (15 mL) followed by addition of Hexanes (60 mL). The slurry was stirred for 5 min, filtered, washed with DCM/hexanes (1:2, 2×10 mL) and dried under vacuum to give the title compound (7.67 g, 80%) as a yellow solid. ¹NMR (500 MHz, DMSO-d₆) δ ppm 0.70 (t, 7.1 Hz, 3H), 0.81 (t, 7.1 Hz, 3H), 1.04-1.27 (m, 8H), 2.74 (s, 2H), 3.73 (s, 3H), 6.91 (s, 1H), 7.01 (s, 1H), 7.52 (dd, J=7.8, 7.2 Hz, 2H), 7.63 (t, J=7.2 Hz, 1H), 7.67 (d, J=7.8 Hz, 2H). EI-LCMS m/z 388 (M⁺+1).

Intermediate G: (3R,5R)-3-butyl-3-ethyl-8-hydroxy-7-methoxy-5-phenyl-2,3,4,5-tetrahydrobenzo[f][1,4]thiazepine 1,1-dioxide, (+)-camphorsulfonate salt

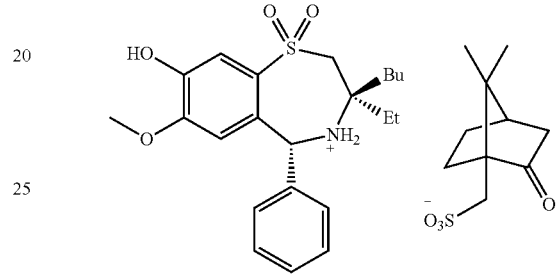

A vessel was charged with (R)-(2-((2-amino-2-ethylhexyl)thio)-4-hydroxy-5-methoxyphenyl)(phenyl)methanone (1.4 g, 3.61 mmol), toluene (8.4 mL) and citric acid (0.035 g, 0.181 mmol, 5 mol %). The mixture was heated to reflux overnight with a Dean-Stark trap to remove water. The mixture was concentrated under reduced pressure to remove solvents. Methanol (14.0 mL) and oxone (2.22 g, 3.61 mmol, 1.0 equiv) were added. The mixture was stirred at gentle reflux for 2 h. The mixture was cooled to ambient temperature, and filtered to remove solids. The filter cake was washed with small amount of Methanol. The filtrate was cooled to 5° C., and treated with sodium borohydride (0.410 g, 10.84 mmol, 3.0 equiv.) in small portions. The mixture was stirred at 5° C. for 2 h and then concentrated to remove the majority of solvents. The mixture was quenched with Water (28.0 mL) and extracted with EtOAc (28.0 mL). The organic layer was washed with brine, and then concentrated to remove solvents. The residue was dissolved in MeCN (14.0 mL) and concentrated again to remove solvents. The residue was dissolved in MeCN (7.00 mL) and MTBE (7.00 mL) at 40° C., and treated with (+)-camphorsulfonic acid (0.839 g, 3.61 mmol, 1.0 equiv.) at 40° C. for 30 min. The mixture was cooled to ambient temperature, stirred for 2 h, and filtered to collect solids. The filter cake was washed with MTBE/MeCN (2:1, 3 mL), and dried at 50° C. to give the title compound (0.75 g, 32% overall yield, 98.6 purity, 97% de, 99.7% ee) as white solids. ¹NMR (400 MHz, CDCl₃) δ ppm 0.63 (s, 3H), 0.88 (t, J=6.9 Hz, 3H), 0.97 (m, 6H), 1.29-1.39 (m, 5H), 1.80-1.97 (m, 6H), 2.08-2.10 (m, 1H), 2.27 (d, J=17.3 Hz, 1H), 2.38-2.44 (m, 3H), 2.54 (b, 1H), 2.91 (b, 1H), 3.48 (d, J=15.4 Hz, 1H), 3.79 (s, 3H), 4.05 (d, J=17.2 Hz, 1H), 6.45 (s, 1H), 6.56 (s, 1H), 7.51-7.56 (m, 4H), 7.68 (s, 1H), 7.79 (b, 2H), 11.46 (b, 1H). EI-LCMS m/z 404 (M$^+$+1 of free base).

Intermediate H: (3R,5R)-3-butyl-3-ethyl-7-methoxy-1,1-dioxido-5-phenyl-2,3,4,5-tetrahydrobenzo[f][1,4]thiazepin-8-yl trifluoromethanesulfonate

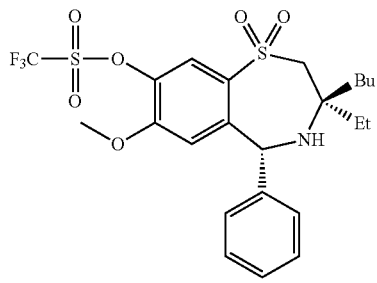

Method 1: A mixture of (3R,5R)-3-butyl-3-ethyl-8-hydroxy-7-methoxy-5-phenyl-2,3,4,5-tetrahydrobenzo[f][1,4]thiazepine 1,1-dioxide, (+)-camphorsulfonate salt (0.5 g, 0.786 mmol), EtOAc (5.0 mL), and 10% of Na$_2$CO$_3$ aqueuous solution (5 mL) was stirred for 15 min. The layers were separated and the aqueous layer was discarded. The organic layer was washed with dilute brine twice, concentrated to remove solvents. EtOAc (5.0 mL) was added and the mixture was concentrated to give a pale yellow solid free base. 1,4-Dioxane (5.0 mL) and pyridine (0.13 mL, 1.57 mmol) were added. The mixture was cooled to 5-10° C. and triflic anhydride (0.199 mL, 1.180 mmol) was added while maintaining the temperature below 15° C. The mixture was stirred at ambient temperature until completion deemed by HPLC (1 h). Toluene (5 mL) and water (5 mL) were added. Layers were separated. The organic layer was washed with water, concentrated to remove solvents. Toluene (1.0 mL) was added to dissolve the residue followed by Isooctane (4.0 mL). The mixture was stirred at rt overnight. The solids was filtered, washed with Isooctane (4.0 mL) to give the title compound (0.34 g, 81%) as slightly yellow solids. $^1$NMR (400 MHz, CDCl$_3$) δ ppm 0.86 (t, J=7.2 Hz, 3H), 0.94 (t, J=7.6 Hz, 3H), 1.12-1.15 (m, 1H), 1.22-1.36 (m, 3H), 1.48-1.60 (m, 2H), 1.86-1.93 (m, 2H), 2.22 (dt, J=4.1 Hz, 12 Hz, 1H), 3.10 (d, J=14.8 Hz, 1H), 3.49 (d, J=14.8 Hz, 1H), 3.64 (s, 3H), 6.11 (s, 1H), 6.36 (s, 1H), 7.38-7.48 (m, 5), 7.98 (s, 1H).
Method 2: A mixture of (R)-3-butyl-3-ethyl-7-methoxy-5-phenyl-2,3-dihydrobenzo[f][1,4]thiazepin-8-yl trifluoromethanesulfonate (0.5 g, 0.997 mmol), ligand (N) (0.078 g, 0.110 mmol) and Ir(COD)$_2$BArF (0.127 g, 0.100 mmol) in DCM (10.0 mL) was purged with nitrogen three times, then hydrogen three times. The mixture was shaken in Parr shaker under 10 Bar of H$_2$ for 24 h. The experiment described above was repeated with 1.0 g (1.994 mmol) input of (R)-3-butyl-3-ethyl-7-methoxy-5-phenyl-2,3-dihydrobenzo[f][1,4]thiazepin-8-yl trifluoromethanesulfonate. The two batches of the reaction mixture were combined, concentrated to remove solvents, and purified by silica gel chromatography (hexanes:EtOAc=9:1) to give the sulfide (O) as slightly yellow oil (0.6 g, 40% yield, 99.7% purity). The oil (0.6 g, 1.191 mmol) was dissolved in TFA (1.836 mL, 23.83 mmol) and stirred at 40° C. H$_2$O$_2$ (0.268 mL, 2.62 mmol) was added slowly over 30 min. The mixture was stirred at 40° C. for 2 h and then cooled to room temperature. Water (10 mL) and toluene (6.0 mL) were added. Layers were separated and the organic layer was washed successively with aqueous sodium carbonate solution and water, and concentrated to dryness. Toluene (6.0 mL) was added and the mixture was concentrated to dryness. The residue was dissolved in toluene (2.4 mL) and isooctane (7.20 mL) was added. The mixture was heated to reflux and then cooled to room temperature. The mixture was stirred at room temperature for 30 min. The solid was filtered and washed with isooctane to give the title compound (0.48 g, 75%).

Intermediate L: (R)-5-((2-amino-2-ethylhexyl)thio)-2-methoxyphenol, di-p-toluoyl-L-tartrate salt

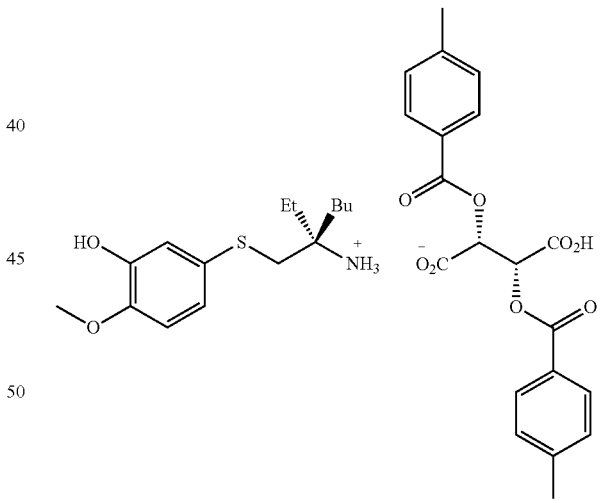

To a mixture of (R)-2-amino-2-ethylhexyl hydrogen sulfate (11.1 g, 49.3 mmol) in water (23.1 mL) was added NaOH (5.91 g, 148 mmol). The mixture was stirred at reflux for 2 h. The mixture was cooled to room temperature and extracted with MTBE (30.8 mL). The extract was washed with brine (22 mL), concentrated under vacuum and treated with methanol (30.8 mL). The mixture was stirred under nitrogen and treated with 3-hydroxy-4-methoxythiophenol (7.70 g, 49.3 mmol). The mixture was stirred under nitrogen at room temperature for 1 h. The mixture was concentrated under vacuum, treated with acetonitrile (154 mL) and then heated to 45° C. To the stirred mixture was added (2R,3R)-2,3-bis((4-methylbenzoyl)oxy)succinic acid (19.03 g, 49.3 mmol). The resultant slurry was stirred at 45° C. After 2 h, the slurry was cooled to room temperature and stirred for 5 h. The solids were filtered, washed twice with acetonitrile (30 mL) and dried to give the title compound (28.0 g, 85%) as white solids. $^1$NMR (400 MHz, DMSO-$d_6$) δ (ppm): 0.70-0.75 (m, 6H), 1.17 (b, 4H), 1.46-1.55 (m, 4H), 2.30 (s, 6H), 3.71 (s, 3H), 5.58 (s, 2H), 6.84 (s, 2H), 6.89 (s, 1H), 7.24 (d, J=11.6 Hz, 4H), 7.76 (d, J=11.6 Hz, 4H).

Intermediate M: (R)-3-butyl-3-ethyl-7-methoxy-5-phenyl-2,3 dihydrobenzo[f][1,4]thiazepin-8-yl trifluoromethanesulfonate

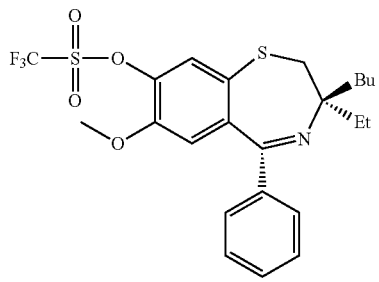

A flask was charged with (R)-(2-((2-amino-2-ethylhexyl)thio)-4-hydroxy-5-methoxyphenyl)(phenyl)methanone (3.5 g, 9.03 mmol), citric acid (0.434 g, 2.258 mmol), 1,4-Dioxane (17.50 mL) and Toluene (17.50 mL). The mixture was heated to reflux with a Dean-Stark trap to distill water azetropically. The mixture was refluxed for 20 h and then cooled to room temperature. EtOAc (35.0 mL) and water (35.0 mL) were added and layers were separated. The organic layer was washed with aqueous sodium carbonate solution and concentrated to remove solvents to give crude imine as brown oil. The oil was dissolved in EtOAc (35.0 mL) and cooled to 0-5° C. To the mixture was added triethylamine (1.888 mL, 13.55 mmol) followed by slow addition of Tf$_2$O (1.831 mL, 10.84 mmol) at 0-5° C. The mixture was stirred at room temperature for 1 h. Water was added and layers were separated. The organic layer was washed with brine, dried over Na$_2$SO$_4$ and concentrated under vacuum. The crude triflate was purified by silica gel chromatography (hexane:EtOAc=90:10) to give the title compound (3.4 g, 75%) as amber oil. $^1$NMR (400 MHz, CDCl$_3$) δ ppm 0.86 (t, J=7.2 Hz, 3H), 0.92 (t, J=7.9 Hz, 3H), 1.19-1.34 (m, 4H), 1.47-1.71 (m, 4H), 3.25 (s, 2H), 3.75 (s, 3H), 6.75 (s, 1H), 7.35-7.43 (m, 3H), 7.48 (s, 1H), 7.54 (d, J=7.6 Hz, 2H).

What is claimed is:

1. A method for preparing the compound

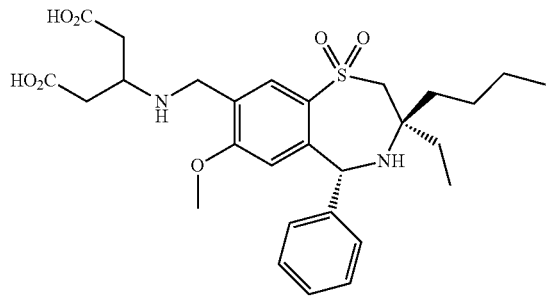 [SMILES: CCCC[C@]1(CC)CS(=O)(=O)c2cc(CNC(CC(=O)O)CC(=O)O)c(OC)cc2[C@@H](c2ccccc2)N1]

comprising the step of preparing the compound

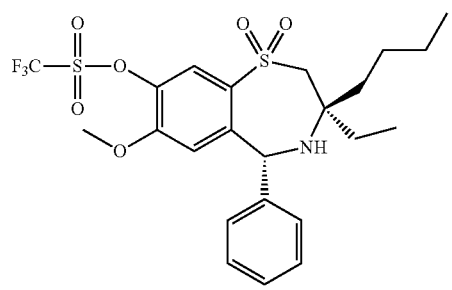 [SMILES: CCCC[C@]1(CC)CS(=O)(=O)c2cc(OS(=O)(=O)C(F)(F)F)c(OC)cc2[C@@H](c2ccccc2)N1]

from 3-hydroxy-4-methoxythiophenol.

2. The method of claim 1 wherein said 3-hydroxy-4-methoxythiophenol is prepared from 2-methoxyphenyl acetate.

3. The method of claim 1 wherein said 3-hydroxy-4-methoxythiophenol is converted to

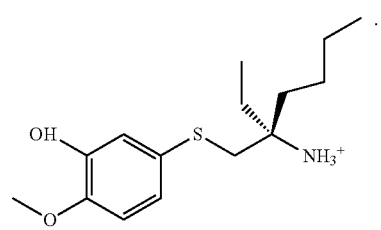 [SMILES: CCCC[C@]([NH3+])(CC)CSc1ccc(OC)c(O)c1]

4. The method of claim 3 wherein the depicted structure is prepared as the corresponding dibenzoyl-L-tartrate salt.

5. The method of claim 3 wherein the depicted structure is prepared as the corresponding di-p-toluoyl-L-tartrate salt.

6. The method of claim 1 wherein said 3-hydroxy-4-methoxythiophenol is converted to

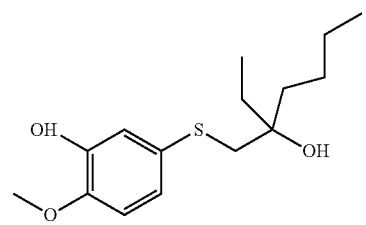 [SMILES: CCCCC(O)(CC)CSc1ccc(OC)c(O)c1]

which is then converted to

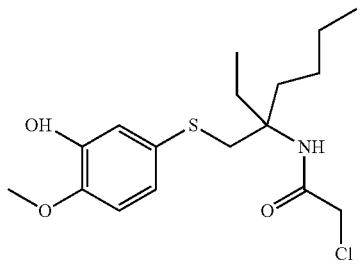 [SMILES: CCCCC(CC)(CSc1ccc(OC)c(O)c1)NC(=O)CCl]

via a Ritter reaction.

7. The method of claim 6 wherein said Ritter reaction uses ClCH$_2$CN.

8. The method of claim 1 wherein said 3-hydroxy-4-methoxythiophenol is converted to

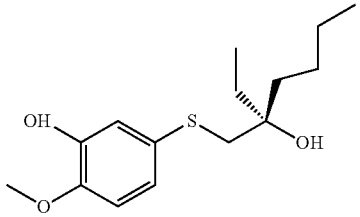

9. The method of claim 8 wherein said conversion includes reaction of said 3-hydroxy-4-methoxythiophenol with (R)-2-ammonio-2-ethylhexyl sulfate.

10. The method of claim 1 wherein said 3-hydroxy-4-methoxythiophenol is converted to

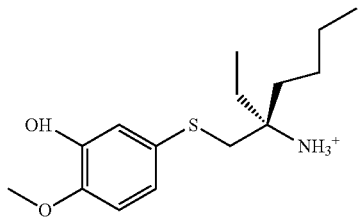 [SMILES: CCCC[C@]([NH3+])(CC)CSc1ccc(OC)c(O)c1]

which is then converted to

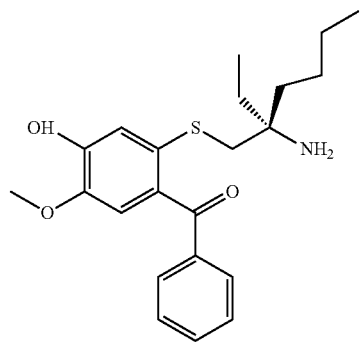 [SMILES: CCCC[C@](N)(CC)CSc1cc(O)c(OC)cc1C(=O)c1ccccc1]

which is then converted to

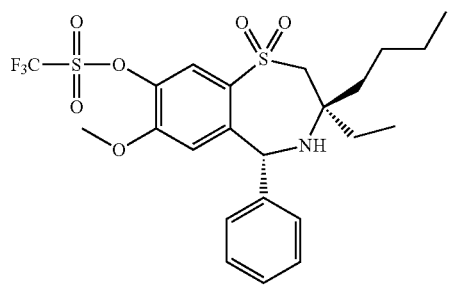 [SMILES: CCCC[C@]1(CC)CS(=O)(=O)c2cc(OS(=O)(=O)C(F)(F)F)c(OC)cc2[C@@H](c2ccccc2)N1]

which is then converted to

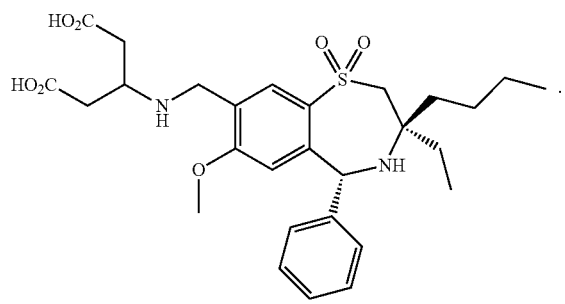 [SMILES: CCCC[C@]1(CC)CS(=O)(=O)c2cc(CNC(CC(=O)O)CC(=O)O)c(OC)cc2[C@@H](c2ccccc2)N1]

* * * * *